US012729249B2

(12) United States Patent
Liang et al.

(10) Patent No.: US 12,729,249 B2
(45) Date of Patent: Sep. 8, 2026

(54) GANODERMA LUCIDUM BETA-GLUCAN EXTRACT, PREPARATION METHOD AND DETECTION METHOD THEREFOR

(71) Applicant: SHAANXI UNIVERSITY OF SCIENCE AND TECHNOLOGY, Xi'an (CN)

(72) Inventors: Chengyuan Liang, Xi'an (CN); Boxin Zhang, Xi'an (CN); Changhua Ke, Xi'an (CN); Shan Yang, Xi'an (CN); Jingjing Zhou, Xi'an (CN); Jinrong Hu, Xi'an (CN); Yuting Liu, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 413 days.

(21) Appl. No.: 18/381,603

(22) Filed: Oct. 18, 2023

(65) Prior Publication Data

US 2024/0132928 A1 Apr. 25, 2024
US 2024/0228674 A9 Jul. 11, 2024

(30) Foreign Application Priority Data

Oct. 19, 2022 (CN) .......................... 202211281114.9

(51) Int. Cl.
*C08B 37/00* (2006.01)
*C12P 19/04* (2006.01)

(52) U.S. Cl.
CPC ...... *C08B 37/0024* (2013.01); *C08B 37/0003* (2013.01); *C12P 19/04* (2013.01)

(58) Field of Classification Search
CPC ... C08B 37/0024; C08B 37/0003; C12P 19/04
See application file for complete search history.

(56) References Cited

FOREIGN PATENT DOCUMENTS

| | | | | |
|---|---|---|---|---|
| CN | 105039459 A | * | 11/2015 | |
| CN | 108976314 A | * | 12/2018 | A61P 37/02 |
| CN | 112979840 A | * | 6/2021 | C07H 3/04 |
| CN | 114805620 A | * | 7/2022 | A61P 37/04 |
| JP | 2012520289 A | * | 9/2012 | A61P 3/10 |

OTHER PUBLICATIONS

Karslioglu et al., Investigation of extraction method effect on yeast beta glucan production, Eurasian J Bio Chem Sci, published Dec. 9, 2021, vol. 4, No. 2, p. 51-55 (Year: 2021).*

Janson, On the History of the Development of Sephadex, Chromatographia, published May 1987, vol. 23, No. 5 (Year: 1987).*

Garcia-Vaquero, Extraction and Yield Optimisation of Fucose, Glucans and Associated Antioxidant Activities from Laminaria digitata by Applying Response Surface Methodology to High Intensity, Mar. Drugs, published 2018, vol. 16, No. 257 (Year: 2018).*

Pubchem Compound Identifier 14798, Sodium Hydroxide, Pubchem, published Oct. 11, 2021 (Year: 2021).* de Jesus et al., Simple and effective purification approach to dissociate mixed water-insoluble α- and β-D-glucans and its application on the medicinal mushroom Fomitopsis betulina, Carbohydrates Polymers, published Nov. 15, 2018, vol. 200, p. 353-360 (Year: 2018).*

Chuang et al., Sacchachitin, a novel chitin-polysaccharide conjugate macromolecule present in Ganoderma lucidum: Purification, composition, and properties, Pharmaceutical Biology, published Oct. 8, 2012, vol. 51, No. 1, p. 84-95 (Year: 2012).*

Megazyme, Mushroom and Yeast Beta-Glucan Assay Procedure, Megazyme, available Feb. 7, 2022 from <https://web.archive.org/web/20220207192715/https://www.megazyme.com/documents/Assay_Protocol/K-YBGL_DATA.pdf> (Year: 2022).*

Xu et al., An extracellular exo-β-(1,3)-glucanase from Pichia pastoris: Purification, characterization, molecular cloning, and functional expression, Protein Expression and Purification, published 2006, vol. 47, No. 1, p. 118-127 (Year: 2006).*

Lachance et al., Purification and partial characterization of an exo-beta-glucanase from the yeast Kluyveromyces aestaurii, Can J Biochem, published 1977, vol. 55, No. 9, Abstract obtained from PubMed <https://pubmed.ncbi.nlm.nih.gov/20206/> (Year: 1977).*

Bilskey et al., A Comparative Analysis of Methods for Quantitation of Sugars during the Corn-to-Ethanol Fermentation Process, SLAS Technology, published 2020, vol. 25, No. 5, p. 494-504 (Year: 2020).*

Cn108976314A, machine traslation obtained from Espacenet. (Year: 2018).*

CN105039459A, machine traslation obtained from Espacenet. (Year: 2015).*

JP2012520289A, machine traslation obtained from Google Patents. (Year: 2012).*

CN114805620A, machine traslation obtained from Espacenet (Year: 2022).*

(Continued)

*Primary Examiner* — David Steadman
*Assistant Examiner* — Scott E. Mulder

(57) ABSTRACT

The present invention provides a *Ganoderma lucidum* β-glucan extract, a preparation method and detection method therefor. The preparation method includes: S1: crushing fruiting bodies of *Ganoderma lucidum*, mixing the crushed fruiting bodies with a solvent, adding trypsin for enzymatic hydrolysis for 0.5-2 h, and separating to obtain a *Ganoderma lucidum* fruiting body filter residue; S2: mixing the *Ganoderma lucidum* fruiting body filter residue with an alkali solution, carrying out ultrasonic extraction with heating, adjusting the pH value of the obtained filtrate to be neutral, and concentrating to obtain a crude *Ganoderma lucidum* polysaccharide; S3: carrying out alcohol precipitation on the crude *Ganoderma lucidum* polysaccharide, separating the obtained precipitate, and freeze-drying to obtain a crude *Ganoderma lucidum* β-glucan extract; and S4: purifying the crude *Ganoderma lucidum* β-glucan extract by glucose gel column chromatography to obtain a *Ganoderma lucidum* β-glucan extract.

2 Claims, 2 Drawing Sheets

(56) References Cited

OTHER PUBLICATIONS

CN112979840A, machine traslation obtained from Espacenet (Year: 2021).*
Yoo et al., Hydrolysis of beta-glucan in oat flour during subcritical-water extraction, Food Chemistry, published Mar. 5, 2020, vol. 308, No. 125670 (Year: 2020).*
Huang et al., Optimization of Alkaline Extraction of Polysaccharides from Ganoderma lucidum and Their Effect on Immune Function in Mice, Molecules, published 2010, vol. 15, p. 3694-3708 (Year: 2010).*
Siu, Isolation and structural characterization of mushroom polysaccharides in relationship with their antioxidant activities, Hong Kong Polytechnic University, published 2015 (Year: 2015).*
Reports of the science of living, Osaka City University, 1987, vol. 35, pp. 1-10.
Trends Food Sci Technol, 2021, vol. 112, pp. 50-57.

* cited by examiner

GANODERMA LUCIDUM BETA-GLUCAN EXTRACT, PREPARATION METHOD AND DETECTION METHOD THEREFOR

This application claims priority to Chinese Patent Application No. 202211281114.9, filed on Oct. 19, 2022, which is incorporated by reference for all purposes as if fully set forth herein.

FIELD OF THE INVENTION

The present invention relates to the technical field of medicines, and specifically to a *Ganoderma lucidum* β-glucan extract, a preparation method and detection method therefor.

DESCRIPTION OF THE RELATED ART

*Ganoderma lucidum* (Curtis) P. Karst. is an umbrella-shaped whole plant of polyporaceae plants *Ganoderma lucidum* (Leyss. ex Fr.) Karst, or *Ganoderma sinense*, with a kidney-shaped, semicircular or approximately round pileus. Since ancient times, it has been a rare Chinese herbal medicine, which was originally wild and mainly grew in Zhejiang, Guangxi, Jiangxi, Hunan and other places. Nowadays, with the improvement of cultivation techniques, it is mainly cultivated. Among others, Shandong has the largest output. With the deepening of research, more biological activities of *Ganoderma lucidum* have been discovered. *Ganoderma lucidum* is mainly used to protect liver and clear away toxic materials, treat diabetes, improve cardiovascular system, prevent aging and improve immunity.

*Ganoderma lucidum* polysaccharides are one of the most effective components in *Ganoderma lucidum*, and are extracted from *Ganoderma lucidum* spores or *Ganoderma lucidum* fruiting bodies. At present, there are more than 200 kinds of *Ganoderma lucidum* polysaccharides isolated, most of which are β-glucan and a few of which are α-glucan. β-glucan is the most active component in *Ganoderma lucidum* polysaccharides, and plays an important role in clinical practice because of its immunomodulatory, anti-tumor, anti-colitis, antibacterial, antiviral and other activities. Therefore, it is of great medical significance to study the preparation, separation, and quantitative detection and analysis of β-glucan.

At present, methods for preparing *Ganoderma lucidum* β-glucan include hot water extraction, ultrasonic extraction, microwave extraction, etc., which have the disadvantages of low extraction efficiency, long extraction time, and a large amount of impurities in the product. Therefore, there is an urgent need for a preparation method of a *Ganoderma lucidum* β-glucan extract with high content.

SUMMARY OF THE INVENTION

An objective of the present invention is to provide a *Ganoderma lucidum* β-glucan extract, a preparation method and detection method therefor. The preparation method is simple, with high product purity and high extraction efficiency. The detection method is simple, rapid, sensitive, and accurate.

The present invention is accomplished through the following technical solutions:

A preparation method for a *Ganoderma lucidum* β-glucan extract, including:

S1: crushing fruiting bodies of *Ganoderma lucidum*, mixing the crushed fruiting bodies with a solvent, adding trypsin for enzymatic hydrolysis for 0.5-2 h, and separating to obtain a *Ganoderma lucidum* fruiting body filter residue;

S2: mixing the *Ganoderma lucidum* fruiting body filter residue with an alkali solution, carrying out ultrasonic extraction with heating, adjusting the pH value of the obtained filtrate to be neutral, and concentrating to obtain a crude *Ganoderma lucidum* polysaccharide;

S3: carrying out alcohol precipitation on the crude *Ganoderma lucidum* polysaccharide, separating the obtained precipitate, and freeze-drying to obtain a crude *Ganoderma lucidum* β-glucan extract; and S4: purifying the crude *Ganoderma lucidum* β-glucan extract by glucose gel column chromatography to obtain a *Ganoderma lucidum* β-glucan extract.

Preferably, in the step S1, the solvent is an ethanol solution, a methanol solution, or an N,N-dimethylformamide solution.

Preferably, in the step S1, the solvent is an ethanol solution.

Preferably, in the step S2, a temperature of the heating is 60° C.-80° C.

Preferably, in the step S2, the alkali solution is a sodium hydroxide solution, and the concentration of the sodium hydroxide solution is 0.01-1 mol/L.

Preferably, the step S3 further includes: adding the crude *Ganoderma lucidum* polysaccharide to 2-5 times volume of 90% ethanol solution, standing at room temperature for 8-12 h for alcohol precipitation, collecting the precipitate, and freeze-drying to obtain the crude *Ganoderma lucidum* β-glucan extract.

Preferably, in the step S4, the purification by chromatography is carried out using 0.1 mol/L NaOH solution as a mobile phase.

A *Ganoderma lucidum* β-glucan extract obtained by the preparation method.

A detection method for a *Ganoderma lucidum* β-glucan extract, including:

preparing standard solutions with different concentrations using a glucose standard substance, carrying out high performance liquid chromatography on the standard solutions with the different concentrations to obtain chromatographic peak areas, and plotting a standard concentration-peak area curve according to the concentrations of the standard solutions and the chromatographic peak areas;

dissolving a *Ganoderma lucidum* β-glucan extract in hydrochloric acid, adding water and pressurizing for hydrolysis, cooling the obtained hydrolysate, and adding a KOH solution to adjust the pH value to 6-7; adding an exo-1,3-beta-glucanase and β-glucosidase solution diluted with a 0.2 mol/L pH 5.2 sodium acetate buffer, mixing evenly, carrying out enzymatic hydrolysis reaction for 1-2 h, and using the obtained hydrolysate as a test solution; and carrying out high performance liquid chromatography on the test solution to obtain a chromatographic peak area, and calculating the content of β-glucan in the *Ganoderma lucidum* β-glucan extract according to the chromatographic peak area and the standard concentration-peak area curve.

Preferably, the *Ganoderma lucidum* β-glucan extract is the *Ganoderma lucidum* β-glucan extract obtained by the above extraction method.

Compared with the prior art, the present invention has the following beneficial effects.

In the method of the present invention, solvent-trypsin pretreatment is used, and β-glucan in *Ganoderma lucidum* is extracted through ultrasonic-assisted hot-alkaline extraction. The present invention integrates the advantages of ultrasonic extraction and hot-alkaline extraction to obtain a higher extraction rate, so that the extraction efficiency is high, the product purity is high, and the method is simple and convenient.

In the present invention, a high pressure-acid-enzyme hydrolysis-HPLC method is established using glucose as a standard substance, to determine the prepared *Ganoderma lucidum* β-glucan extract. The hydrolysis mode of the enzyme is that after the enzyme is bonded to the substrate, the glucose glycosidic bonds of the substrate are cleaved in sequence from the non-reducing end of β-glucan, to release single glucose residues. The detection method, i.e., the HPLC method, is based on the principle that components entering the chromatographic column at the same time are distributed repeatedly between the two phases of the chromatographic column along with the mobile phase due to the different functions of dissolution, adsorption, permeation or ion exchange between the mobile phase and the stationary phase. Due to the different moving speeds of the components in the chromatographic column, the components are separated from each other after passing through a certain length of the chromatographic column. The components flow out of the chromatographic column in sequence, and enter a signal detector, and peak values of the components are displayed on a recorder or data processing device. Through the qualitative analysis according to retention times and the quantitative analysis using an external standard method according to peak areas, the method is simple, rapid, sensitive and accurate, and has broad application prospects, providing an effective and reliable analytical method for the determination of *Ganoderma lucidum* β-glucan with various biological activities.

DETAILED DESCRIPTION OF THE PREFERRED EMBODIMENTS

Figure 1:
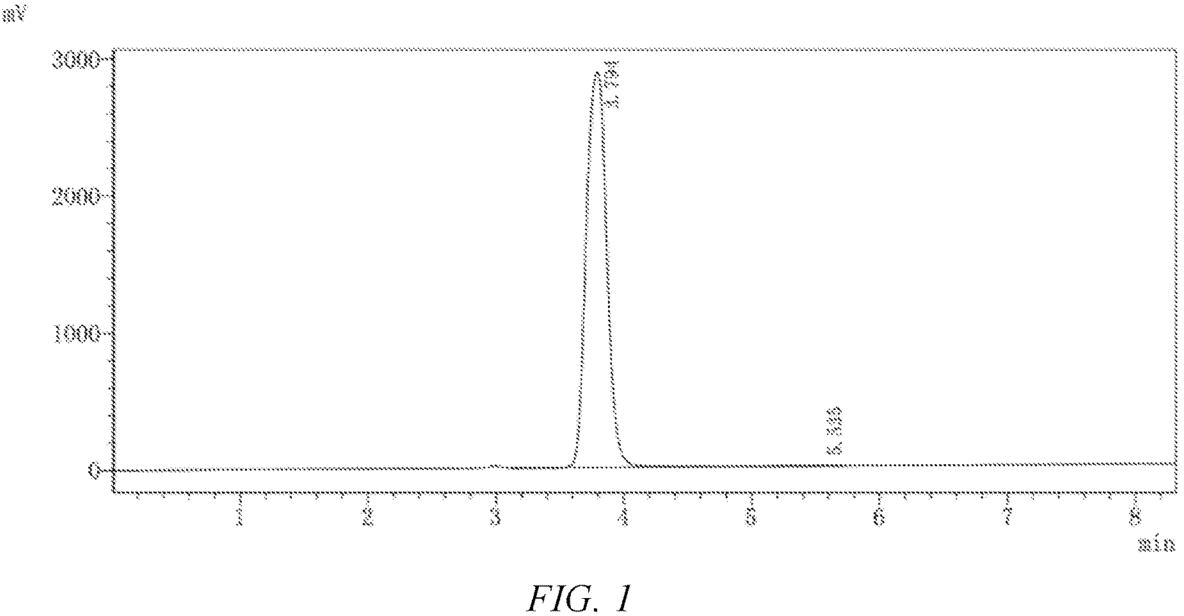
FIG. 1 is a chromatogram of a glucose reference substance.

For a further understanding of the present invention, the present invention will be described below through examples. It should be understood that these descriptions are merely used for further explaining the features and advantages of the present invention and are not intended to limit the claims of the present invention.

The present invention discloses a preparation method and an efficient and rapid detection method for a *Ganoderma lucidum* β-glucan extract with high content, where β-glucan in *Ganoderma lucidum* is extracted through ethanol-trypsin pretreatment combined with ultrasonic-assisted hot-alkaline extraction and purified by DEAE Sephadex® A-25 glucan gel column chromatography, and the content of β-glucan in the prepared *Ganoderma lucidum* β-glucan extract is determined by a high pressure-acid-enzyme hydrolysis-HPLC method. Methodological investigation shows that the method has high sensitivity, good stability, good reproducibility, and high detection accuracy.

The preparation method is specifically as follows.

S1. Ethanol-Trypsin Pretreatment of *Ganoderma lucidum* Fruiting Bodies

*Ganoderma lucidum* fruiting bodies are weighed, crushed, sieved, and placed in a test tube with a stopper. An ethanol solution with a certain concentration is added. The test tube is placed on a vortex mixer for mixing. Then, trypsin is added for enzymatic hydrolysis for 0.5-2 h to remove impurities such as oils and fats, pigments, and proteins in the fruiting bodies. The reaction solution is centrifuged and filtered. The filtrate is discarded to obtain a *Ganoderma lucidum* fruiting body filter residue.

S2. Hot-Alkaline Extraction of Crude *Ganoderma lucidum* Polysaccharides

The *Ganoderma lucidum* fruiting body filter residue is placed in a round bottom flask. A NaOH solution is added. The flask is placed in an ultrasonic cleaner for ultrasonic treatment at a temperature of 60° C. to 80° C. After the ultrasonic treatment is completed, the solution is centrifuged and filtered to obtain a first filtrate. The obtained filter residue is subjected to the above steps again for hot-alkaline extraction, centrifuging, and filtering, to obtain a second filtrate. The two filtrates are combined. The pH value is adjusted to neutral with a hydrochloric acid solution. The obtained neutral extract is placed in a rotary evaporator and concentrated to ¼ of the original volume under vacuum.

S3. Alcohol Precipitation to Obtain a Crude *Ganoderma lucidum* β-Glucan Extract 2-5 times volume of 90% ethanol solution is added to the concentrate obtained in the step S2, allowed to stand at room temperature for 8-12 h for alcohol precipitation, centrifuged, and filtered. The supernatant is discarded, and the precipitate is collected and freeze-dried to obtain the crude *Ganoderma lucidum* β-glucan extract.

S4. Purification of *Ganoderma lucidum* β-Glucan

The crude *Ganoderma lucidum* β-glucan extract is dissolved in a certain amount of distilled water and centrifuged. The supernatant is collected and purified by DEAE Sephadex® A-25 glucose gel column chromatography using 0.1 mol/L NaOH solution as a mobile phase. The components containing β-glucan are collected, concentrated, and freeze-dried to obtain high-content, high-purity *Ganoderma lucidum* β-glucan.

The detection method is specifically as follows.

S1: Preparation of Standard Solution

A glucose standard is accurately weighed, and high-purity water is added to prepare a standard stock solution.

S2. Preparation of Test Solution

*Ganoderma lucidum* β-glucan is accurately weighed and placed in a test tube with a stopper. A certain amount of hydrochloric acid is added. The test tube is placed on a vortex mixer for even mixing. The test tube is placed in a thermostat water bath for 20-40 min, and is periodically placed in a mixer for a period of time to ensure that β-glucan is fully dissolved. Then the evenly mixed sample is transferred to a Schott® bottle, and high-purity water is added. The solution is shaken until uniform, and then the Schott® bottle is placed in an autoclave for hydrolysis. After hydrolysis, the Schott® bottle is taken out and cooled to room temperature, and a KOH solution is added to adjust the pH value to 6-7.

The high-pressure hydrolysate is transferred to a volumetric flask. The test tube is washed with a 0.2 mol/L pH 5.2 sodium acetate buffer. The wash solution is added to the volumetric flask, diluted to make up the volume, and filtered. The filtrate is taken. A certain amount of an exo-1,3-beta-glucanase and β-glucosidase solution diluted with a 0.2 mol/L pH 5.2 sodium acetate buffer is added, mixed evenly on a mixer, and reacted at 40° C. for 1-2 h. The obtained hydrolysate is transferred to a volumetric flask and diluted to make up the volume, to obtain the test solution.

S3. Plotting of Standard Curve 1.0 mL, 2.0 mL, 4.0 mL, 5.0 mL and 10.0 mL of the standard solution obtained in the step S1 are respectively placed in a 25 mL volumetric flask, and high-purity water is added to make up the volume to the mark, to obtain standard solutions with concentrations of 20, 40, 80, 100 and 200 μg/mL. The standard solutions are filtered by a 0.45 μm microporous filter membrane. 20 μL of each of the filtrates is accurately taken and injected into a high performance liquid chromatograph in sequence. A standard curve is plotted.

S4. Determination of Sample Content

The test solution in the step S2 is filtered by a 0.45 μm microporous filter membrane. Then 20 μL of the filtrate is accurately taken and injected into a high performance liquid chromatograph. After elution, the content and extraction rate of β-glucan in *Ganoderma lucidum* are calculated according to the standard concentration-peak area curve.

Conditions of the high performance liquid chromatography in the steps S2 and S3 are as follows:

- chromatographic column: Shodex® SH1011 column (8.0 mm×300 mm, 6 μm)
- mobile phase: high-purity water
- flow rate: 0.5 mL/min
- column temperature: 80° C.
- temperature of differential refractive index detector: 35° C.
- sample size: 20 μL Methodological Investigation (1) Precision Test According to the above method, a glucose standard solution with a concentration of 60 μg/mL is prepared. Under the same conditions, the glucose standard solution with the known concentration is injected repeatedly for 6 times. Retention times and peak areas of the solutions are measured, and relative standard deviation (RSD) values (which should be less than 3%) are calculated to investigate the precision of the instrument.

(2) Repeatability Test

Under the same conditions, the test solution obtained in the above process is injected repeatedly for 6 times. Retention times and peak areas of the solutions are measured, and RSD values (which should be less than 3%) are calculated to investigate the repeatability of the instrument.

(3) Stability Test

The test solution prepared in the above process is allowed to stand for 0, 2, 4, 8, 12, and 24 h respectively, and then injected according to the above chromatographic conditions to test the stability of the sample.

(4) Recovery Test 0.16 mL, 0.20 mL, and 0.24 mL of the standard stock solution are respectively placed in a 2 mL volumetric flask, and high-purity water is added to make up the volume to the mark, to obtain three standard glucose solutions with concentrations of 40 μg/mL, 50 μg/mL, and 60 μg/mL respectively. The three glucose standard solutions with different concentrations are respectively added into the test solution with the known concentration, and are injected for determination under the same conditions. The determination is carried out three times in parallel for each concentration.

Instruments used in the present invention are as follows:

Shimadzu-LabSolutions (Shimadzu LC-16, Japan); RID-20A differential refractive index detector (Shimadzu, Japan); BSA224S Electronic balance with an accuracy of 1/10000 g (Sartorius Stedim (Shanghai) Trading Co., Ltd.); ES1035A Electronic balance with an accuracy of 1/10000 g (TianJin D&T Transducer Technology Co., Ltd.); GL2202-1SCN Electronic balance with an accuracy of 1/100 g (Sartorius Stedim (Shanghai) Trading Co., Ltd.); KQ-300DE Ultrasonic cleaner (Kunshan Ultrasonic Instruments Co., Ltd.); RV-S Rotary evaporator (Wuxi Xinghaiwang Biochemical Equipment Co., Ltd.); JC-XW-I Vortex mixer (Qingdao Juchuang Century Environmental Protection Technology Co., Ltd.); LS-75HD Autoclave (Jiangyin Binjiang Medical); YB-2000A Crusher (Yongkang Sufeng Industry and Trade Co., Ltd.); SJIA-10N Freeze Dryer (Ningbo Shuangjia Instrument Co., Ltd.).

The reagents and materials used in the present invention are as follows:

food-grade trypsin (purity: 99%, Zhejiang Fuxuan Biotechnology Co., Ltd.); DEAE-Sephadex® A-25 (purity: 99%, Shanghai Zeye Biotechnology Co., Ltd.); Glucose standard (purity: HPLC≥99.6%, National Institute of Metrology, China); *Ganoderma lucidum* polysaccharide (purity: GC≥95%, National Institute of Metrology, China); high-purity water: self-made in laboratory sodium acetate buffer (3 mol/L, pH 5.2, sterile, Leagene Biotechnology); exo-1,3-beta-glucanase and β-glucosidase (BR, Puyi (Shanghai) Biotechnology Co., Ltd.).

Example 1

A preparation method for a *Ganoderma lucidum* β-glucan extract was provided, including the following steps.

1. Ethanol-Trypsin Pretreatment of *Ganoderma lucidum* Fruiting Bodies 10 g of *Ganoderma lucidum* fruiting bodies was weighed, crushed, sieved through a 50 mesh screen, and placed in a test tube with a stopper. 15 mL of an 80% ethanol solution was added. The test tube was placed on a vortex mixer and mixed for 20 min. Then, 1 g of trypsin was added for enzymatic hydrolysis for 1 h to remove impurities such as oils and fats, pigments, and proteins in the fruiting bodies. The reaction solution was centrifuged at 5000 r/min for 20 min and filtered. The filtrate was discarded to obtain a *Ganoderma lucidum* fruiting body filter residue.

2. Hot-Alkaline Extraction of Crude *Ganoderma lucidum* Polysaccharides

The *Ganoderma lucidum* fruiting body filter residue was placed in a 100 mL round bottom flask. 20 mL of a NaOH solution (0.1 mol/L) was added. The flask was placed in an ultrasonic cleaner for ultrasonic treatment at a power of 380 W and a temperature of 70° C. for 40 min. After the ultrasonic treatment was completed, the solution was centrifuged at 5000 r/min for 20 min and filtered to obtain a first filtrate. The obtained filter residue was subjected to the above steps again for hot-alkaline extraction, centrifuging, and filtering, to obtain a second filtrate. The two filtrates were combined. The pH value was adjusted to neutral with a hydrochloric acid solution (0.2 mol/L). The obtained neutral extract was placed in a rotary evaporator and concentrated to 1/4 of the original volume under vacuum.

3. Alcohol Precipitation to Obtain a Crude *Ganoderma lucidum* β-Glucan Extract 3 times volume of 90% ethanol solution was added to the concentrate obtained in the step S2, allowed to stand at room temperature for 10 h for alcohol precipitation, centrifuged at 5000 r/min for 20 min, and filtered. The supernatant was discarded, and the precipitate was collected and freeze-dried to obtain the crude *Ganoderma lucidum* β-glucan extract.

4. Purification of *Ganoderma lucidum* β-Glucan

The crude *Ganoderma lucidum* β-glucan extract was dissolved in 50 mL of distilled water and centrifuged. The supernatant was collected and purified by DEAE Sephadex® A-25 glucan gel column chromatography using 0.1 mol/L NaOH solution as a mobile phase. The components containing β-glucan were collected, concentrated, and freeze-dried to obtain a high-content, high-purity *Ganoderma lucidum* β-glucan extract.

Specific steps of the detection method for a *Ganoderma lucidum* β-glucan extract were as follows.

1: Preparation of Standard Solution

A glucose standard was accurately weighed, and high-purity water was added to prepare a 500 μg/mL solution, i.e., a standard stock solution.

2. Preparation of Test Solution 1.0000 g of *Ganoderma lucidum* β-glucan was accurately weighed and placed in a 50 mL test tube with a stopper. 1 mL of hydrochloric acid was added. The test tube was placed on a vortex mixer for even mixing. The test tube was placed in a thermostat water bath at 40° C. for 30 min, and was placed in a mixer for 15 s every 10 min to ensure that β-glucan was fully dissolved. Then the evenly mixed sample was transferred to a 100 mL Schott® bottle, and high-purity water was added to make up the volume to 40 mL. The solution was shaken until uniform, and then the Schott® bottle was placed in an autoclave at 121° C. for hydrolysis for 60 min. After hydrolysis, the Schott® bottle was taken out and cooled to room temperature, and a KOH solution (2 mol/L) was added to adjust the pH value to 7.

The high-pressure hydrolysate was transferred to a 50 mL volumetric flask. The test tube was washed with a 0.2 mol/L pH 5.0 sodium acetate buffer. The wash solution was added to the volumetric flask, diluted to make up the volume, and filtered. 0.1 mL of the filtrate was taken. 5 mL of an exo-1,3-beta-glucanase and β-glucosidase solution diluted with a 0.2 mol/L pH 5.0 sodium acetate buffer was added, mixed evenly on a mixer, and reacted at 40° C. for 1.5 h. The obtained hydrolysate is transferred to a 50 mL volumetric flask and diluted to make up the volume, to obtain the test solution.

3. Plotting of Standard Curve 1.0 mL, 2.0 mL, 4.0 mL, 5.0 mL and 10.0 mL of the standard solution obtained in the step S1 were respectively placed in a 25 mL volumetric flask, and high-purity water was added to make up the volume to the mark, to obtain standard solutions with concentrations of 20, 40, 80, 100 and 200 μg/mL. The standard solutions were filtered by a 0.45 μm microporous filter membrane. 20 μL of each of the filtrates was accurately taken and injected into a high performance liquid chromatograph in sequence. The obtained HPLC chromatogram was shown in FIG. 1. The measured peak areas of the standard solutions with the series of concentrations were shown in Table 1.

TABLE 1

Concentrations and peak areas of glucose standard

| No. | Concentration (μg/mL) | Peak area (A) |
|---|---|---|
| 1 | 20 | 290449 |
| 2 | 40 | 552429 |
| 3 | 80 | 1076389 |
| 4 | 100 | 1338369 |
| 5 | 200 | 2648269 |

Figure 2:
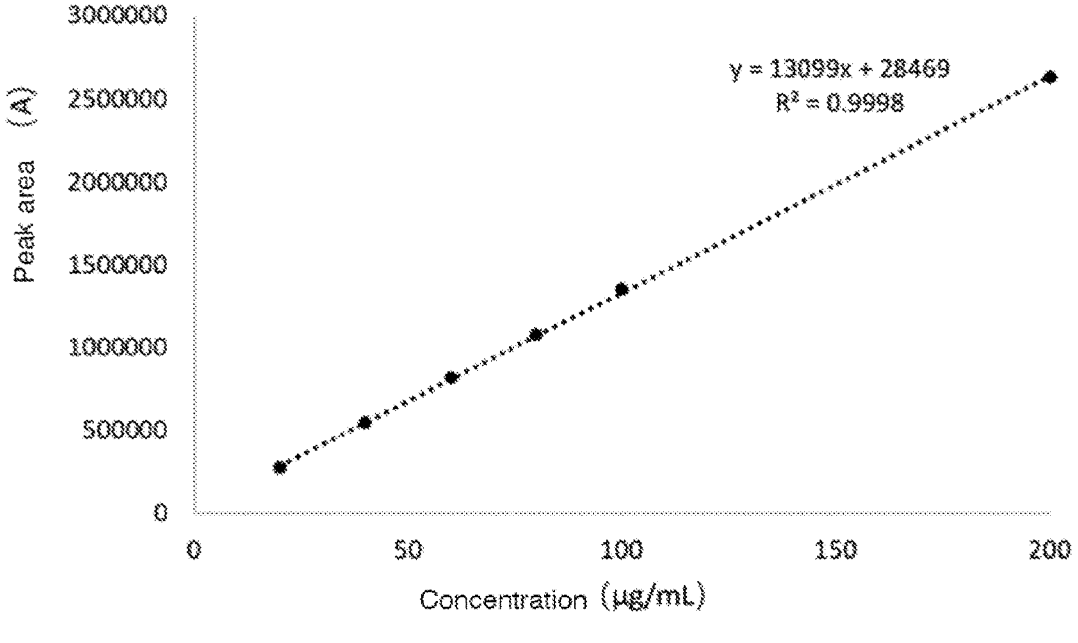
FIG. 2 is a standard curve of glucose.
Figure 3:
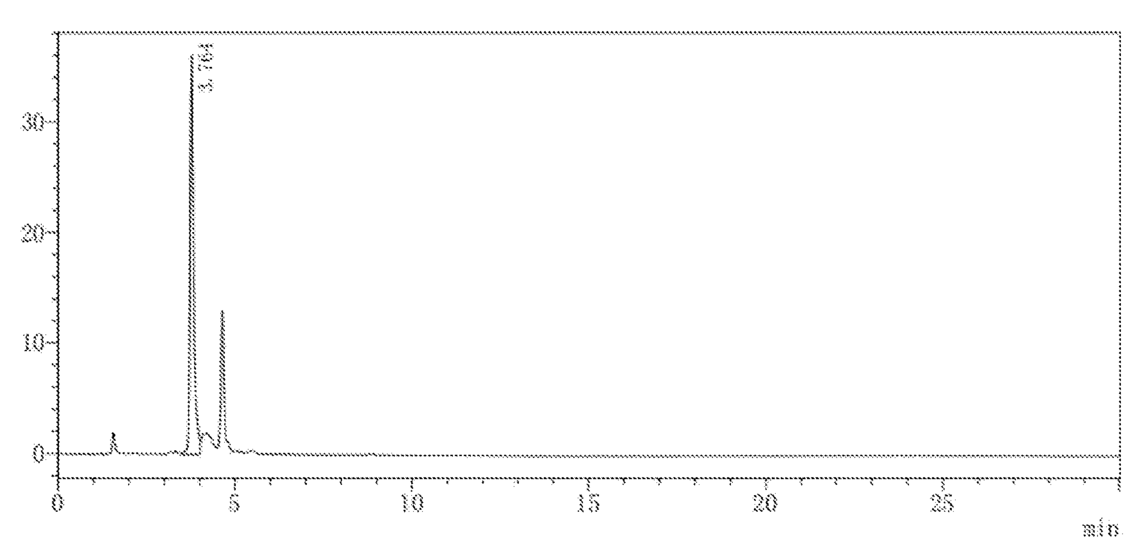
FIG. 3 is a chromatogram of a *Ganoderma lucidum* β-glucan sample in Example 1.

According to Table 1, a standard curve was obtained with concentration as X axis and peak area as Y axis, as shown in FIG. 2. An equation of the glucose standard curve was Y=13099X+28469, with a correlation coefficient $R^2$=0.9998, and having a good linear relationship.

4. Determination of Sample Content

The test solution obtained in the step 2 was filtered through a 0.45 μm microporous filter membrane. Then 20 μL of the filtrate was accurately taken and injected into a high performance liquid chromatograph for elution to obtain a chromatogram 3. As obtained through calculation according to the standard concentration-peak area curve, the content of β-glucan in 1 g of the sample was 0.918 g, and the extraction yield was 91.8%.

Methodological Investigation:

(1) Precision Test

According to the above method, a glucose standard solution with a concentration of 60 μg/mL was prepared. Under the same conditions, the glucose standard solution with the known concentration was injected repeatedly for 6 times. Retention times and peak areas of the solutions were measured, and RSD values were calculated. See Table 2. The calculated RSD values were all less than 3%, indicating good precision of parallel injection of the equipment.

TABLE 2

Retention times and peak areas in the precision test

| Number of times of sample injection | Retention time (min) | Peak area (A) |
|---|---|---|
| 1 | 3.792 | 32032860 |
| 2 | 3.774 | 32433800 |
| 3 | 3.750 | 31007560 |
| 4 | 3.803 | 32100073 |
| 5 | 3.687 | 31870997 |
| 6 | 3.787 | 32692400 |
| RSD (%) | 1.130 | 1.809 |

(2) Repeatability Test

Under the same conditions, the test solution obtained in the above process was injected repeatedly for 6 times. The measured retention times and peak areas of the solutions were analyzed, and RSD values were calculated. See Table 3. The calculated RSD values were all less than 3%, indicating good reproducibility of this method.

TABLE 3

Retention times and peak areas in the repeatability test

| Number of times of sample injection | Retention time (min) | Peak area (A) |
|---|---|---|
| 1 | 3.764 | 262014 |
| 2 | 3.737 | 266138 |
| 3 | 3.627 | 263919 |

TABLE 3-continued

Retention times and peak areas in the repeatability test

| Number of times of sample injection | Retention time (min) | Peak area (A) |
|---|---|---|
| 4 | 3.720 | 265977 |
| 5 | 3.768 | 260020 |
| 6 | 3.744 | 260015 |
| RSD (%) | 1.394 | 1.053 |

(3) Stability Test

The test solution prepared in the above process was allowed to stand for 0, 2, 4, 8, 12, and 24 h respectively, and then injected according to the above chromatographic conditions. The measured retention times and peak areas of the solutions were analyzed, and RSD values were calculated. See Table 4. The calculated RSD values were all less than 3%, indicating that the *Ganoderma lucidum* polysaccharide sample solution has good stability at room temperature within 24 h.

TABLE 4

Retention times and peak areas in the stability test

| Time (h) | Retention time (min) | Peak area (A) |
|---|---|---|
| 0 | 3.726 | 229092 |
| 2 | 3.795 | 229034 |
| 4 | 3.747 | 227433 |
| 8 | 3.796 | 223026 |
| 12 | 3.682 | 222965 |
| 24 | 3.710 | 221430 |
| RSD (%) | 1.232 | 1.514 |

(4) Recovery Test 0.16 mL, 0.2 mL, and 0.24 mL of the standard stock solution were respectively placed in a 2 mL volumetric flask, and high-purity water was added to make up the volume to the mark, to obtain three standard glucose solutions with concentrations of 40 μg/mL, 50 μg/mL, and 60 μg/mL respectively. The three glucose standard solutions with different concentrations were respectively added into the test solution with the known concentration, and were injected for determination under the same conditions. The determination was carried out three times in parallel for each concentration. The measured retention times and peak areas of the solutions were analyzed, and RSD values were calculated. The results were shown in Table 5. The calculated RSD values were all less than 3%. The recovery rate with addition of the standard was 98.7% to 104.525%, indicating that the method was accurate.

TABLE 5

Recovery rate with addition of the standard

| No. | Concentration of test solution (μg/mL) | Addition amount (μg/mL) | Measured amount (μg) | Recovery rate (%) | Average recovery rate (%) | RSD (%) |
|---|---|---|---|---|---|---|
| 1 | 50 | 40 | 89.784 | 99.460 | | |
| 2 | 50 | 40 | 91.810 | 104.525 | | |
| 3 | 50 | 40 | 90.414 | 101.036 | | |
| 4 | 50 | 50 | 100.630 | 101.260 | | |
| 5 | 50 | 50 | 101.278 | 102.556 | 100.897 | 1.761 |
| 6 | 50 | 50 | 99.350 | 98.700 | | |
| 7 | 50 | 60 | 110.152 | 100.245 | | |
| 8 | 50 | 60 | 110.454 | 100.757 | | |
| 9 | 50 | 60 | 109.722 | 99.537 | | |

Example 2

Conditions for pretreatment of *Ganoderma lucidum* fruiting bodies were optimized and compared according to the following method.

1. Pretreatment of *Ganoderma lucidum* Fruiting Bodies 10 g of *Ganoderma lucidum* fruiting bodies was weighed, crushed, sieved through a 50 mesh screen, and placed in each test tube with a stopper. 15 mL of 80% ethanol, methanol, and N,N-dimethylformamide (DMF) solutions were added respectively to the test tubes. Each of the test tubes was placed on a vortex mixer and mixed for 20 min. Then, 1 g of trypsin was added for enzymatic hydrolysis for 1 h to remove impurities such as oils and fats, pigments, and proteins in the fruiting bodies. The reaction solution was centrifuged at 5000 r/min for 20 min and filtered. The filtrate was discarded to obtain a *Ganoderma lucidum* fruiting body filter residue.

2. Hot-Alkaline Extraction of Crude *Ganoderma lucidum* Polysaccharides

A method for preparing crude *Ganoderma lucidum* polysaccharides through hot-alkaline extraction was the same as the specific preparation steps in Example 1.

3. Alcohol Precipitation to Obtain a Crude *Ganoderma lucidum* β-Glucan Extract

A method for obtaining the crude *Ganoderma lucidum* β-glucan extract through alcohol precipitation was the same as the specific preparation steps in Example 1.

4. Purification of *Ganoderma lucidum* β-Glucan

A method for purifying the *Ganoderma lucidum*-glucan was the same as the specific preparation steps in Example 1.

5. Preparation of Test Solution

The purified β-glucan was treated according to the specific detection steps in Example 1, to obtain three test solutions.

6. Determination of Sample Content

The three test solutions obtained in the step 5 were each filtered through a 0.45 μm microporous filter membrane. Then 20 μL of each of the filtrates was accurately taken and injected into a high performance liquid chromatograph for elution. According to the standard concentration-peak area curve, the obtained peak areas was converted into concentrations. The results were shown in Table 6.

TABLE 6

Optimization of conditions for pretreatment of *Ganoderma lucidum* fruiting bodies

| Solvent | Content (g/g) | Extraction rate (%) |
|---|---|---|
| Ethanol | 0.918 | 91.8 |
| Methanol | 0.877 | 87.7 |
| DMF | 0.895 | 89.5 |

The results show that the pretreatment of *Ganoderma lucidum* fruiting bodies with ethanol and trypsin was more efficient in extracting *Ganoderma lucidum* β-glucan. Therefore, ethanol was selected as the pretreatment reagent.

Example 3

Comparison of extraction temperatures in hot-alkaline extraction of crude *Ganoderma lucidum* polysaccharides was carried out according to the following method.

1. Ethanol-Trypsin Pretreatment of *Ganoderma lucidum* Fruiting Bodies

A method for ethanol-trypsin pretreatment of *Ganoderma lucidum* fruiting bodies was the same as the specific preparation steps in Example 1.

2. Hot-Alkaline Extraction of Crude *Ganoderma lucidum* Polysaccharides

The *Ganoderma lucidum* fruiting body filter residue was placed in a 100 mL round bottom flask. 20 mL of a NaOH solution (0.1 mol/L) was added. The flask was placed in an ultrasonic cleaner for ultrasonic treatment at a power of 380 W and respectively at temperatures of 60° C., 70° C., and 80° C. for 40 min. After the ultrasonic treatment was completed, the solution was centrifuged at 5000 r/min for 20 min and filtered to obtain a first filtrate. The obtained filter residue was subjected to the above steps again for hot-alkaline extraction, centrifuging, and filtering, to obtain a second filtrate. The two filtrates were combined. The pH value was adjusted to neutral with a hydrochloric acid solution (0.2 mol/L). The obtained neutral extract was placed in a rotary evaporator and concentrated to ¼ of the original volume under vacuum.

3. Alcohol Precipitation to Obtain a Crude *Ganoderma lucidum* β-Glucan Extract

A method for obtaining the crude *Ganoderma lucidum* β-glucan extract through alcohol precipitation was the same as the specific preparation steps in Example 1.

4. Purification of *Ganoderma lucidum* β-Glucan

A method for purifying the *Ganoderma lucidum* β-glucan was the same as the specific preparation steps in Example 1.

5. Preparation of Test Solution

The purified β-glucan was treated according to the specific detection steps in Example 1, to obtain three test solutions.

6. Determination of Sample Content

The three test solutions obtained in the step 5 were each filtered through a 0.45 μm microporous filter membrane. Then 20 μL of each of the filtrates was accurately taken and injected into a high performance liquid chromatograph for elution. According to the standard concentration-peak area curve, the obtained peak areas was converted into concentrations. The results were shown in Table 7.

TABLE 7

Contents of β-glucan extracted from *Ganoderma lucidum* at different temperatures

| Temperature of ultrasonic treatment (° C.) | Content (g/g) | Extraction rate (%) |
|---|---|---|
| 60 | 0.882 | 88.2 |
| 70 | 0.918 | 91.8 |
| 80 | 0.912 | 91.2 |

The results show that when the temperature of ultrasonic treatment was 70° C. in the extraction of crude *Ganoderma lucidum* polysaccharides through ultrasonic-assisted hot-alkaline extraction, the efficiency of preparing *Ganoderma lucidum* β-glucan was higher. Therefore, 70° C. was selected as the temperature of ultrasonic treatment.

Example 4

Comparison of different alkaline solution concentrations in hot-alkaline extraction of crude *Ganoderma lucidum* polysaccharides was carried out according to the following method.

1. Ethanol-Trypsin Pretreatment of *Ganoderma lucidum* Fruiting Bodies

A method for ethanol-trypsin pretreatment of *Ganoderma lucidum* fruiting bodies was the same as the specific preparation steps in Example 1.

2. Hot-Alkaline Extraction of Crude *Ganoderma lucidum* Polysaccharides

The *Ganoderma lucidum* fruiting body filter residue was placed in 100 mL round bottom flasks. 20 mL of a 0.01 mol/L NaOH solution, 20 mL of a 0.1 mol/L NaOH solution, and 20 mL of a 1 mol/L NaOH solution were respectively added to the flasks. The flasks were each placed in an ultrasonic cleaner for ultrasonic treatment at a power of 380 W and a temperature of 60° C.-80° C. for 40 min. After the ultrasonic treatment was completed, the solution was centrifuged at 5000 r/min for 20 min and filtered to obtain a first filtrate. The obtained filter residue was subjected to the above steps again for hot-alkaline extraction, centrifuging, and filtering, to obtain a second filtrate. The two filtrates were combined. The pH value was adjusted to neutral with a hydrochloric acid solution (0.2 mol/L). The obtained neutral extract was placed in a rotary evaporator and concentrated to ¼ of the original volume under vacuum.

3. Alcohol Precipitation to Obtain a Crude *Ganoderma lucidum* β-Glucan Extract

A method for obtaining the crude *Ganoderma lucidum* β-glucan extract through alcohol precipitation was the same as the specific preparation steps in Example 1.

4. Purification of *Ganoderma lucidum* β-Glucan

A method for purifying the *Ganoderma lucidum* β-glucan was the same as the specific preparation steps in Example 1.

5. Preparation of Test Solution

The purified β-glucan was treated according to the specific detection steps in Example 1, to obtain three test solutions.

6. Determination of Sample Content

The three test solutions obtained in the step 5 were each filtered through a 0.45 μm microporous filter membrane. Then 20 μL of each of the filtrates was accurately taken and injected into a high performance liquid chromatograph for elution. According to the standard concentration-peak area curve, the obtained peak areas was converted into concentrations. The results were shown in Table 8.

TABLE 8

Contents of β-glucan extracted from *Ganoderma lucidum* at different alkaline solution concentrations

| Concentration of NaOH solution (mol/L) | Content (g/g) | Extraction rate (%) |
|---|---|---|
| 0.01 | 0.853 | 85.3 |
| 0.1 | 0.918 | 91.8 |
| 1 | 0.890 | 89.0 |

The results show that when the concentration of NaOH solution used in the extraction of crude *Ganoderma lucidum* polysaccharides through ultrasonic-assisted hot-alkaline extraction was 0.1 mol/L, the efficiency of preparing *Ganoderma lucidum* β-glucan was higher. Therefore, the 0.1 mol/L NaOH solution was selected as the extraction solution.

What is claimed is:

1. A method for preparing a *Ganoderma lucidum* β-glucan extract, consisting of:

step 1: crushing fruiting bodies of *Ganoderma lucidum*, mixing the crushed fruiting bodies with an ethanol solution, adding trypsin for enzymatic hydrolysis for 0.5-2 h, and separating to obtain a *Ganoderma lucidum* fruiting body filter residue;

step 2: mixing the *Ganoderma lucidum* fruiting body filter residue with 0.1 mol/L sodium hydroxide (NaOH) solution, carrying out ultrasonic extraction at 70° C., adjusting the pH value of the obtained filtrate to be neutral, and concentrating to obtain a crude *Ganoderma lucidum* polysaccharide;

step 3: adding the crude *Ganoderma lucidum* polysaccharide to 2-5 times volume of 90% ethanol solution, letting a resulted mixture stand at room temperature for 8-12 h for alcohol precipitation, collecting a precipitate, and freeze-drying to obtain a crude *Ganoderma lucidum* β-glucan extract; and step 4: purifying the crude *Ganoderma lucidum* β-glucan extract by an ion exchange chromatography column using 0.1 mol/L NaOH solution as a mobile phase to obtain the *Ganoderma lucidum* β-glucan extract.

2. A method for detecting a *Ganoderma lucidum* β-glucan extract, consisting of:

crushing fruiting bodies of *Ganoderma lucidum*, mixing the crushed fruiting bodies with an ethanol solution, adding trypsin for enzymatic hydrolysis for 0.5-2 h, and separating to obtain a *Ganoderma lucidum* fruiting body filter residue;

mixing the *Ganoderma lucidum* fruiting body filter residue with a 0.1 mol/L sodium hydroxide (NaOH) solution, carrying out ultrasonic extraction at 70° C., adjusting the pH value of the obtained filtrate to be neutral, and concentrating to obtain a crude *Ganoderma lucidum* polysaccharide;

adding the crude *Ganoderma lucidum* polysaccharide to 2-5 times volume of 90% ethanol solution, letting a resulted mixture stand at room temperature for 8-12 h for alcohol precipitation, collecting a precipitate, and freeze-drying the precipitate to obtain a crude *Ganoderma lucidum* β-glucan extract;

purifying the crude *Ganoderma lucidum* β-glucan extract by an ion exchange chromatography column using 0.1 mol/L NaOH solution as a mobile phase to obtain the *Ganoderma lucidum* β-glucan extract, preparing standard solutions with different concentrations using glucose or a compound containing glucose or a glucose moiety, carrying out high performance liquid chromatography on the standard solutions with the different concentrations to obtain chromatographic peak areas, and plotting a standard concentration-peak area curve according to the concentrations of the standard solutions and the chromatographic peak areas;

dissolving the *Ganoderma lucidum* β-glucan extract in hydrochloric acid, adding water and hydrolyzing at a pressure over standard-pressure, cooling the obtained hydrolysate, and adding a potassium hydroxide (KOH) solution to adjust the pH value to 6-7; adding an exo-1,3-beta-glucanase and β-glucosidase solution diluted with a 0.2 mol/L pH 5.2 sodium acetate buffer, mixing evenly, carrying out enzymatic hydrolysis reaction for 1-2 h, and using the obtained hydrolysate as a test solution; and carrying out high performance liquid chromatography on the test solution to obtain a chromatographic peak area, and calculating the content of β-glucan in the *Ganoderma lucidum* β-glucan extract according to the chromatographic peak area and the standard concentration-peak area curve.

* * * * *